US00PP12906P2

(12) United States Plant Patent
Vandenberg et al.

(10) Patent No.: US PP12,906 P2
(45) Date of Patent: Sep. 3, 2002

(54) CHRYSANTHEMUM PLANT NAMED 'YOROANOKE'

(75) Inventors: Cornelis P. Vandenberg, Salinas, CA (US); Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 81 days.

(21) Appl. No.: 09/774,363

(22) Filed: Feb. 1, 2001

(51) Int. Cl.[7] ..... A01H 5/00
(52) U.S. Cl. ..... Plt./297

(58) Field of Search ..... Plt./297

*Primary Examiner*—Bruce R. Campell
*Assistant Examiner*—Anne Marie Grünberg
(74) *Attorney, Agent, or Firm*—C. A. Whealy

(57) ABSTRACT

A distinct cultivar of Chrysanthemum plant named 'Yoroanoke', characterized by its upright and uniformly mounded plant habit; strong and moderately vigorous growth habit; dark green and glossy foliage; uniform flowering response; early flowering, eight-week response time; freely flowering habit; daisy-type inflorescences that are about 5.4 cm in diameter; lavender pink ray florets and bright yellow disc florets; and excellent postproduction longevity with plants maintaining good substance and color for at least three weeks in an interior environment.

1 Drawing Sheet

BACKGROUND OF THE INVENTION

The present Invention relates to a new and distinct cultivar of Chrysanthemum plant, botanically known as *Chrysanthemum×morifolium* and hereinafter referred to by the name 'Yoroanoke'.

The new Chrysanthemum is a product of a planned breeding program conducted by the Inventors in Salinas, Calif. The objective of the breeding program is to create new potted Chrysanthemum cultivars that are suitable for year-round production with uniform plant growth habit, good vigor, desirable inflorescence form and floret colors, fast response time, and excellent postproduction longevity.

The new Chrysanthemum originated from a cross made by the Inventors in October, 1994, in Salinas, Calif., of the Chrysanthemum cultivar Monterey, disclosed in U.S. Plant Pat. No. 7,753, as the female, or seed, parent with the Chrysanthemum cultivar Rage, disclosed in U.S. Plant Pat. No. 8,770, as the male, or pollen, parent. The new Chrysanthemum was discovered and selected by the Inventors as a single flowering plant within the progeny of the stated cross grown in a controlled environment in Salinas, Calif. The selection of this plant was based on its uniform plant growth habit, vigor, desirable inflorescence form and floret colors, fast response time, and excellent postproduction longevity.

Asexual reproduction of the new Chrysanthemum by vegetative tip cuttings was first conducted in Fort Myers, Fla. in February, 1997. Asexual reproduction by cuttings has shown that the unique features of this new Chrysanthemum are stable and reproduced true to type in successive generations.

SUMMARY OF THE INVENTION

The cultivar Yoroanoke has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Yoroanoke'. These characteristics in combination distinguish 'Yoroanoke' as a new and distinct Chrysanthemum:

1. Upright and uniformly mounded plant habit.
2. Strong and moderately vigorous growth habit.
3. Dark green and glossy foliage.
4. Uniform flowering response.
5. Typically grown as a center-budded or natural spray-type.
6. Early flowering, eight-week response time.
7. Freely flowering.
8. Daisy-type inflorescences that are about 5.4 cm in diameter.
9. Lavender pink ray florets and bright yellow disc florets.
10. Excellent postproduction longevity with plants maintaining good substance and color for at least three weeks in an interior environment.

Plants of the new Chrysanthemum can be compared to plants of the female parent, the cultivar Monterey. In side-by-side comparisons conducted by the Inventors in Salinas, Calif., plants of the new Chrysanthemum differ from plants of the cultivar Monterey in the following characteristics:

1. Plants of the new Chrysanthemum are more outwardly spreading than plants of the cultivar Monterey.
2. Plants of the new Chrysanthemum flower about one week earlier than plants of the cultivar Monterey.
3. Ray floret color of the new Chrysanthemum is darker pink than ray floret color of the cultivar Monterey.
4. Inflorescences of the new Chrysanthemum produce pollen whereas inflorescences of the cultivar Monterey produce little to no pollen.

Plants of the new Chrysanthemum can be compared to plants of the male parent, the cultivar Rage. In side-by-side comparisons conducted by the Inventors in Salinas, Calif., plants of the new Chrysanthemum differ from plants of the cultivar Rage in the following characteristics:

1. Plants of the new Chrysanthemum are more outwardly spreading than plants of the cultivar Rage.
2. Plants of the new Chrysanthemum flower more uniformly than plants of the cultivar Rage.
3. Plants of the new Chrysanthemum flower about two to three days earlier than plants of the cultivar Rage.
4. Ray floret color of the new Chrysanthemum is lavender pink whereas ray floret color of the cultivar Rage is red.

Plants of the new Chrysanthemum can be compared to plants of the Chrysanthemum cultivar Yonashville, disclosed in U.S. Plant Pat. No. 11,795. In side-by-side comparisons conducted by the Inventors in Salinas, Calif., plants of the new Chrysanthemum differ from plants of the cultivar Yonashville in the following characteristics:

1. Plants of the new Chrysanthemum are more outwardly spreading than plants of the cultivar Yonashville.
2. The crown of the new Chrysanthemum is mounded whereas the crown of the cultivar Yonashville is flat.
3. Plants of the new Chrysanthemum have smaller inflorescences than plants of the cultivar Yonashville.
4. Ray floret color of the new Chrysanthemum is lighter than ray floret color of the cultivar Yonashville.

Plants of the new Chrysanthemum can also be compared to plants of the Chrysanthemum cultivar Davis, disclosed in U.S. Plant Pat. No. 7,325. In side-by-side comparisons conducted by the Inventors in Salinas, Calif., plants of the new Chrysanthemum differ from plants of the cultivar Davis in the following characteristics:

1. Plants of the new Chrysanthemum are stronger than plants of the cultivar Davis.
2. Plants of the new Chrysanthemum flower about one week earlier than plants of the cultivar Davis.
3. Plants of the new Chrysanthemum flower more uniformly than plants of the cultivar Davis.
4. Ray floret color of the new Chrysanthemum is lighter than ray floret color of the cultivar Davis.
5. Inflorescences of the new Chrysanthemum produce less pollen than inflorescences of the cultivar Davis.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which accurately describe the colors of the new Chrysanthemum.

The photograph at the top of the sheet comprises a top perspective view of a typical flowering plant of 'Yoroanoke' grown a natural spray-type.

The photograph at the bottom of the sheet comprises a close-up view of typical inflorescences of 'Yoroanoke' grown as a natural spray-type.

DETAILED BOTANICAL DESCRIPTION

In the following description, color references are made to The Royal Horticultural Society Colour Chart except where general terms of ordinary dictionary significance are used. The following observations and measurements describe plants grown and flowered during the autumn in Salinas, Calif., in a fiberglass-covered greenhouse and under conditions which approximate those generally used in commercial potted Chrysanthemum production. During the production of these plants, the following conditions were measured: day temperatures, 21 to 27° C.; night temperatures, 17 to 19° C.; and light levels, 4,000 to 6,000 foot-candles. Four unrooted cuttings were directly stuck in 15-containers, exposed to long day/short night conditions, and pinched once about 14 days later. At that time, the photoinductive short day/long night treatments were started. Plants used for this description were grown as natural spray-types. Measurements and numerical values represent averages of typical flowering plants.

Botanical classification: *Chrysanthemum×morifolium* cultivar Yoroanoke.

Commercial classification: Daisy-type potted Chrysanthemum.

Parentage:

*Female, or seed, parent.*—*Chrysanthemum×morifolium* cultivar Monterey, disclosed in U.S. Plant Pat. No. 7,753.

*Male, or pollen, parent.*—*Chrysanthemum×morifolium* cultivar Rage, disclosed in U.S. Plant Pat. No. 8,770.

Propagation:

*Type.*—Terminal tip cuttings.

*Time to intitiate roots.*—About four days at 21° C.

*Time to produce a rooted cutting.*—About ten days at 21° C.

*Root description.*—Fibrous and well-branched.

Plant description:

*Appearance.*—Herbaceous daisy-type potted Chrysanthemum typically grown as a center-budded or natural spray-type. Stems upright and outwardly spreading giving a uniformly mounded appearance to the plant. Freely branching, about four lateral branches develop after removal of terminal apex (pinching); dense and full plants. Moderate vigor.

*Plant height.*—About 30 cm.

*Plant width.*—About 48 cm.

*Lateral branches.*—Length: About 26 cm. Diameter: About 4 mm. Internode length: About 1.5 cm. Strength: Strong. Texture: Pubescent. Color: Darker than 144A to 146A.

*Foliage description.*—Arrangement: Alternate. Quantity of leaves per lateral stem: About 15. Length: About 7.3 cm. Width: About 5.1 cm. Apex: Cuspidate to mucronate. Base: Attenuate to truncate. Margin: Palmately lobed, sinuses between lateral lobes parallel to divergent. Texture: Upper and lower surfaces with very fine pubescence; veins prominent on lower surface. Color: Young foliage, upper surface: Darker and more green than 147A; glossy. Young foliage, lower surface: Darker than 147B. Mature foliage, upper surface: Darker and more green than 147A; glossy. Mature foliage, lower surface; Darker than 147B. Venation, upper surface: 147A to 147B. Venation, lower surface: 147B. Petiole length: About 1.7 cm. Petiole diameter: About 2.5 mm. Petiole color: 146B to 146C.

Inflorescence description:

*Appearance.*—Daisy-type inflorescence form with elongated oblong-shaped ray florets. Infloresences borne on terminals above foliage. Disk and ray florets arranged acropetally on a capitulum. Not fragrant. Typically grown as a center-budded or natural spray-type.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering; plants exposed to two weeks of long day/short night conditions followed by photoinductive short day/long night conditions flower about eight weeks later.

*Postproduction longevity.*—Inflorescences maintain good color and substance for at least three weeks in an interior environment.

*Quantity of inflorescences.*—Freely flowering, about 9 inflorescences develop per lateral stem, or about 36 inflorescences per plant.

*Inflorescence bud.*—Height: About 5 mm. Diameter: About 7.5 mm. Color: 143A.

*Inflorescence size.*—Diameter: About 5.4 cm. Depth (height): About 1.2 cm. Diameter of disc: About 1.5 cm. Receptacle diameter: About 6 mm.

*Ray florets.*—Shape: Elongated-oblong. Orientation: Initially upright, then about 90° from vertical or perpendicular to peduncle. Aspect: Initially incurved, then reflexed. Length: About 2.6 cm. Width: About 9 mm. Corolla tube length: About 3 mm. Apex: Acute, emarginate or cuspidate. Base: Attenuate; short corolla tube. Margin: Entire. Texture: Smooth, glabrous, satiny. Number of ray florets per inflorescence: About 27 arranged in one or two rows. Color: When opening, upper surface: 75A to 77C or slightly darker than 75A to 77C with overtones of 77B. When opening, lower surface: 155D underlain with 75A; overall tonality, 75C to 75D. Fully opened, upper surface: 75A to 77C or slightly darker than 75A to 77C with overtones of 77B. Fully opened, lower surface: 155D underlain with 75A; overall tonality, 75D.

*Disc florets.*—Arrangement: Massed at center of receptacle. Shape: Tubular, elongated. Apex: Five-pointed. Length: About 6 mm. Width: Apex, about 2 mm; base, about 1 mm. Number of disc florets per inflorescence: About 173. Color: Immature: 145A to 154A. Mature: Apex: 9A. Mid-section: 145D. Base: 155D.

*Peduncles.*—Length: First peduncle: About 5.5 cm. Fourth peduncle: About 7.6 cm. Seventh peduncle: About 10.2 cm. Diameter: About 2 mm. Angle to vertical: About 45° from vertical. Strength: Strong, flexible. Color: 144A to 146A.

*Reproductive organs.*—Androecium: Present on disc florets only. Anther color: 12A. Pollen amount: Moderate. Pollen color: 15A. Gynoecium: Present on both ray and disc florets.

*Seed.*—Seed production has not been observed.

Disease resistance: Resistance to pathogens common to Chrysanthemums has not been observed on plants grown under commercial greenhouse conditions.

It is claimed:

1. A new and distinct cultivar of Chrysanthemum plant named 'Yoroanoke', as illustrated and described.

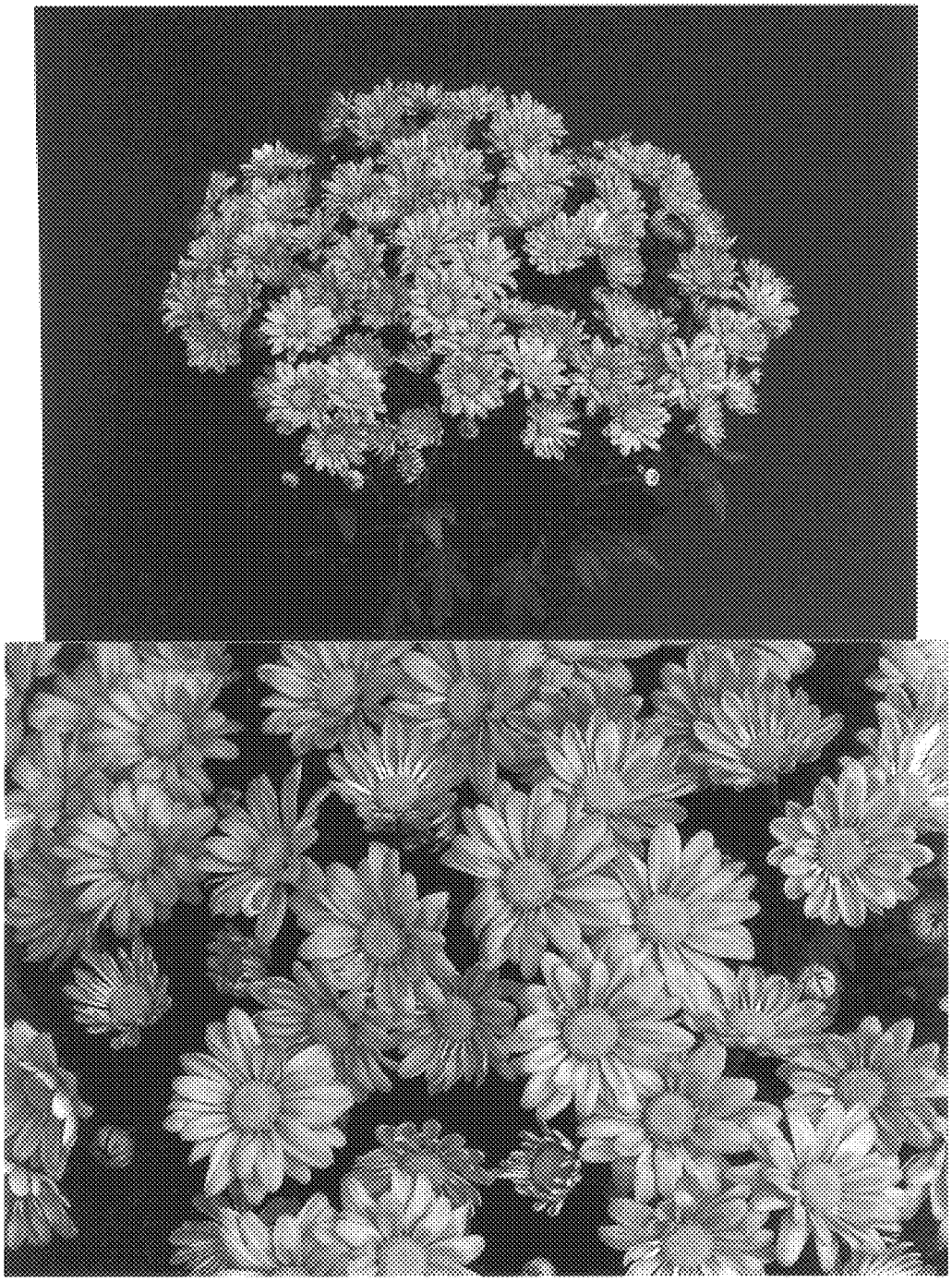

* * * * *